United States Patent [19]

Cooper et al.

[11] Patent Number: 5,817,135
[45] Date of Patent: Oct. 6, 1998

[54] RATE-RESPONSIVE PACEMAKER WITH NOISE-REJECTING MINUTE VOLUME DETERMINATION

[75] Inventors: Daniel Cooper, Hauguenau, France; Saul E. Greenhut, Aurora, Colo.; Chih-ming James Chiang, Phoenix, Ariz.; Tibor A. Nappholz, Englewood, Colo.; Bruce Steinhaus, Flagstaff, Ariz.

[73] Assignee: Pacesetter, Inc., Sylmar, Calif.

[21] Appl. No.: 848,968

[22] Filed: May 2, 1997

[51] Int. Cl.⁶ .............................. A61N 1/362; A61N 1/365
[52] U.S. Cl. ................................................. 607/17; 607/19
[58] Field of Search .................... 607/17, 18, 19

[56] References Cited

U.S. PATENT DOCUMENTS 4,901,725  2/1990  Nappholz et al. .
5,074,303  12/1991  Hauck ........................................ 607/17
5,318,597  6/1994  Hauck et al. .............................. 607/20
5,441,523  8/1995  Nappholz .
5,487,753  1/1996  MacCarter et al. .
5,562,711  10/1996  Yerich et al. .
5,562,712  10/1996  Steinhaus et al. .
5,578,064  11/1996  Prutchi .
5,626,622  5/1997  Cooper ....................................... 607/18

FOREIGN PATENT DOCUMENTS 9320889  10/1993  WIPO .

Primary Examiner—William E. Kamm
Assistant Examiner—Carl H. Layno
Attorney, Agent, or Firm—Gottlieb, Rackman & Reisman, P.C.

[57] ABSTRACT

A rate responsive implantable pacemaker generates a metabolic demand parameter such as a thoracic impedance which is converted into a corresponding metabolic indicated parameter. During the conversion, intermediate parameters, such as either tidal volume and respiration rate, or a derivative of the metabolic demand parameter are used by a cross-check circuit to insure that artefacts due for example to stroke volume noise are eliminated. The peak limiter is used to limit the metabolic indicated rate to an acceptable range. Both protection circuits use fuzzy logic components.

9 Claims, 11 Drawing Sheets

Adaptive Low-Pass Filter: Time Domain Impulse Response

Adaptive Low-Pass Filter: Frequency Domain Response

CROSS-CHECK 142: INPUT MEMBERSHIP FUNCTIONS

CROSS-CHECK 142: CONFIDENCE RULE BASE

RATE-RESPONSIVE PACEMAKER WITH NOISE-REJECTING MINUTE VOLUME DETERMINATION

| RATE-RESPONSIVE PACEMAKER WITH RAPID MINUTE VOLUME DETERMINATION | 08/850,557 | 5/2/97 |
|---|---|---|
| RATE-RESPONSIVE PACEMAKER WITH MINUTE VOLUME DETERMINATION AND EMI PROTECTION | 08/850,529 | 5/2/97 |
| RATE-RESPONSIVE PACEMAKER WITH EXERCISE RECOVERY USING MINUTE VOLUME DETERMINATION | 08/850,692 | 5/2/97 |

BACKGROUND OF THE INVENTION

1. Field of the Invention

This invention relates to rate-responsive pacemakers and, more particularly, to pacemakers that employ a minute volume metabolic demand sensor as a metabolic rate indication, said sensor operating fast to thereby insure that the pacemaker reacts accurately to changes in the level of activity while ensuring immunity to noise artifact.

2. Description of the Prior Art

Many attempts have been made to control the heart rate of a pacemaker patient so that it will duplicate the intrinsic heart rate of a healthy person both when the patient is at rest and when the patient is involved in various levels of exercise. Metabolic demand related parameters heretofore proposed for controlling the pacing rate include the QT interval, respiration rate, venous oxygen saturation, stroke volume, venous blood temperature, and minute volume or ventilation, among others. (The terms minute ventilation and minute volume are used interchangeably). In addition, the use of mechanical and electrical sensors which detect patient motion have also been explored in such attempts at achieving improved rate-responsiveness. Of the various parameters available, it has been found that pacemakers using minute volume as a parameter for controlling pacing rate are particularly advantageous.

However, a problem with these types of pacers has been that the minute ventilation sensors using thoracic impedance has had trouble with arm motion artifacts as well as stroke volume artifacts.

A further problem is that changes in a patient's physiologic conditions may result in dramatic changes in thoracic impedance which may cause pacing at the maximum rate for long periods of time, causing discomfort and lack of well-being for patients.

OBJECTIVES AND SUMMARY OF THE INVENTION

In view of the above mentioned disadvantages of the prior art, it is an objective of the present invention to provide a pacemaker which dynamically responds to the instantaneous physical level of activity of a patient and adjusts its pulse rate accordingly.

A further objective is to provide a metabolic rate responsive pacemaker which is immune to noise, such as arm motion artifacts, as well as stroke volume (related to the heart rate) artifact.

Another objective is to provide a pacemaker containing a safety algorithm which prevents pacing at the very high rates for extended period of time, either due to patients' physiological changes or noisy signals.

Other objectives and advantages of the invention shall become apparent from the following description. Briefly, a pacemaker constructed in accordance with this invention includes sensing means for sensing a metabolic demand parameter of the patient indicative of his or her instantaneous physical activity. Preferably, the metabolic demand parameter is minute volume which can be determined, for example, from impedance measurements. Minute volume has been found to be an accurate representation of the physical activity and the corresponding blood flow and oxygen demand of a patient. This parameter is converted into a corresponding metabolic indicated rate (MIR), which rate may be used to define the interval between the pacer pulses. Detectors to check for noise signals such as arm motion and stroke volume are used in this conversion process. The mapping of minute volume to metabolic indicated rate (MIR), preferably, uses a preselected curve which may be, for example, an exponential curve, or other monotonic curves. Finally, a peak rate protection feature is also used. The resulting rate is then used to calculate an optimal paced pulse interval.

DETAILED DESCRIPTION OF THE INVENTION

Figure 1:
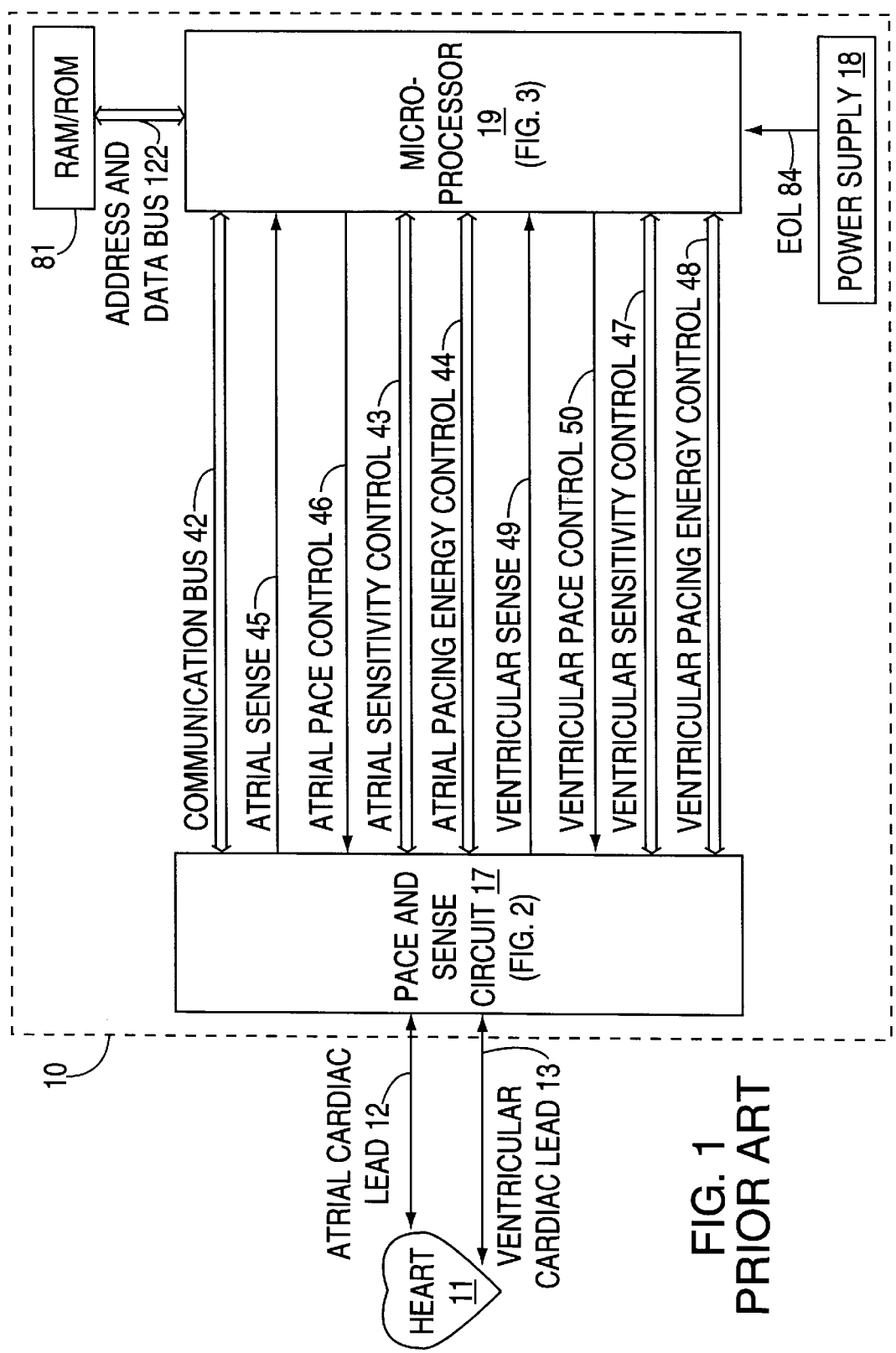
FIG. 1 shows a block diagram of a pacemaker constructed in accordance with this invention.

Details of a pacemaker in accordance with the present invention are shown in FIGS. 1–6. FIG. 1 shows a block diagram of the pacemaker. The pacemaker 10 is designed to be implanted in a patient and is connected by leads 12 and 13 to a patient's heart 11 for sensing and pacing the heart 11 as described for example in U.S. Pat. No. 5,441,523 by T. Nappholz, entitled FORCED ATRIOVENTRICULAR SYNCHRONY DUAL CHAMBER PACEMAKER, and incorporated herein by reference. Briefly, the atrial cardiac lead 12 extends into the atrium of the heart 11 and the ventricular cardiac lead 13 extends into the ventricle of the heart 11. Leads 12 and 13 are used for both sensing electrical activity in the heart and for applying pacing pulses to the heart. The pacemaker 10 includes a pace and sense circuit 17 for the detection of analog signals from leads 12 and 13 and for the delivery of pacing pulses to the heart; a microprocessor 19 which, in response to numerous inputs received form the pace and sense circuit 17, performs operations to generate different control and data outputs to the pace and sense circuit 17; and a power supply 18 which provides a voltage supply to the pace and sense circuit 17 and the microprocessor 19 by electrical conductors (not shown). The microprocessor 19 is connected to a random access memory/read only memory unit 81 by an address and data bus 122. A low power signal line 84 is used to provide to the microprocessor 19 a logic signal indicative of a low energy level of the power supply 18. The microprocessor 19 and the pace and sense circuit 17 are connected to each other by a number of data and control lines including a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
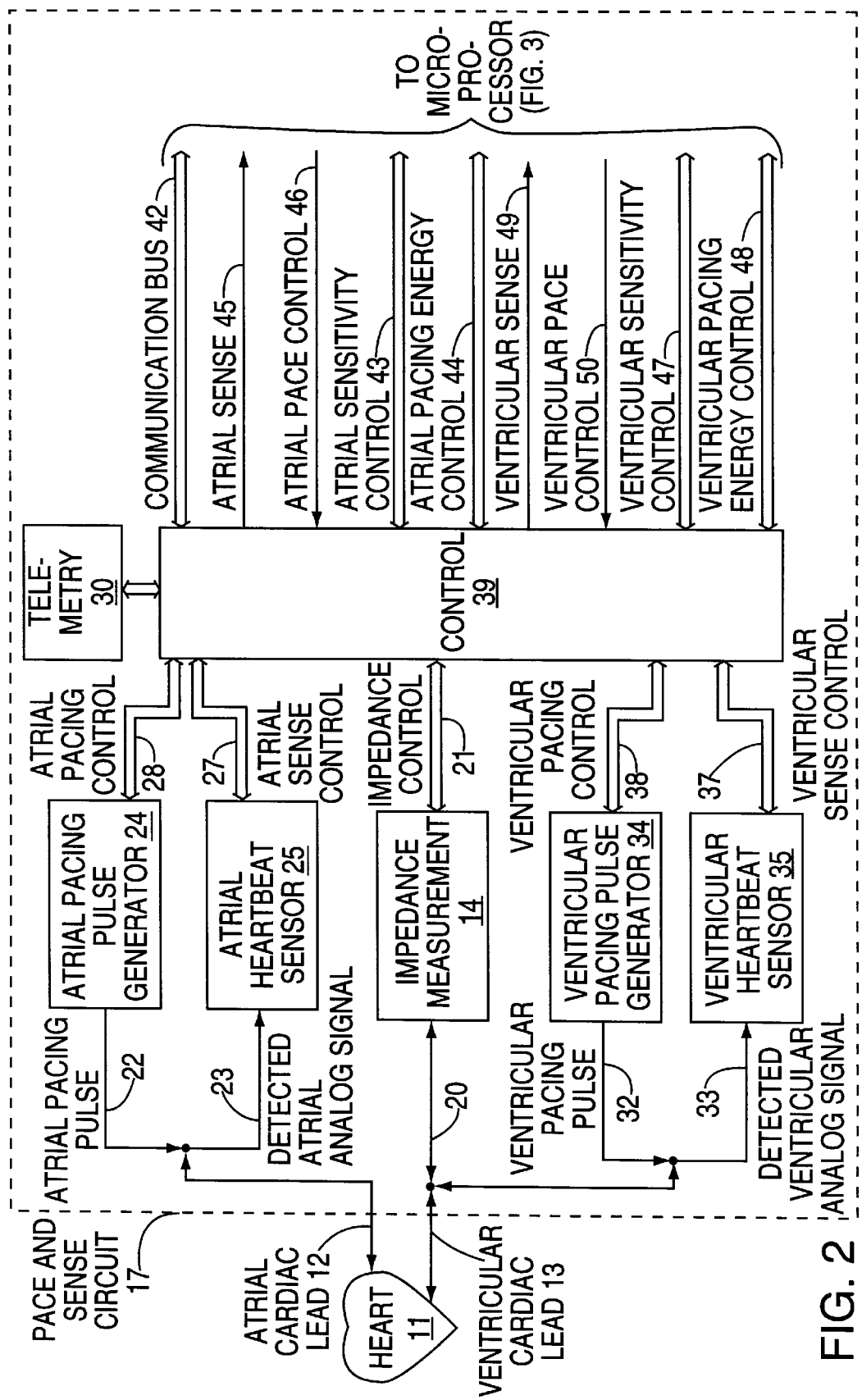
FIG. 2 shows a block diagram of the pace and sense circuit for the pacemaker of FIG. 1.

FIG. 2 shows details of the pace and sense circuit 17. The circuit 17 includes an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 also includes an impedance measurement circuit 14 for measuring a physiological parameter indicative of the patient's metabolic demand. The pace and sense circuit 17 also includes a control block 39 which is interfaced to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control signal on a control bus 27 and an input ventricular sense control signal on a control bus 37, respectively, from the control block 39. These control signals are used to set the sensitivity of the respective sensors.

The atrial pacing pulse generator circuit 24 receives from the control block 39, via an atrial pacing control bus 28, an atrial pace control signal and an atrial pacing energy control signal to generate an atrial pacing pulse 22 at appropriate times. Similarly, the ventricular pacing pulse generator circuit 34 receives from the control block 39, via a ventricular pacing control bus 38, a ventricular pace control signal and a ventricular pacing energy control signal to generate a ventricular pacing pulse 32. The atrial and ventricular pace control signal determine the respective timing of atrial and ventricular pacing that take place, while the atrial and ventricular pacing energy control inputs determine the respective magnitudes of the pulse energies.

The pacemaker 10 makes an impedance measurement when the microprocessor 19 sends a signal on the impedance control bus 21 to activate the impedance measurement circuit 14. The impedance measurement circuit 14 then applies a current to the ventricular cardiac lead 13 via lead 20 and measures a voltage resulting from the applied current, as discussed in more detail below. These current and voltage signals define an impedance characteristic of the patient's metabolic demand, and moire particularly, of the instantaneous minute volume. This instantaneous minute volume is then filtered and further modified by subtracting from it a long term average value, as discussed below. The resulting parameter is the minute volume parameter.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the Model 9600 Network Programmer manufactured by Telectronics of Englewood, Colo., U.S.A.

Figure 3:
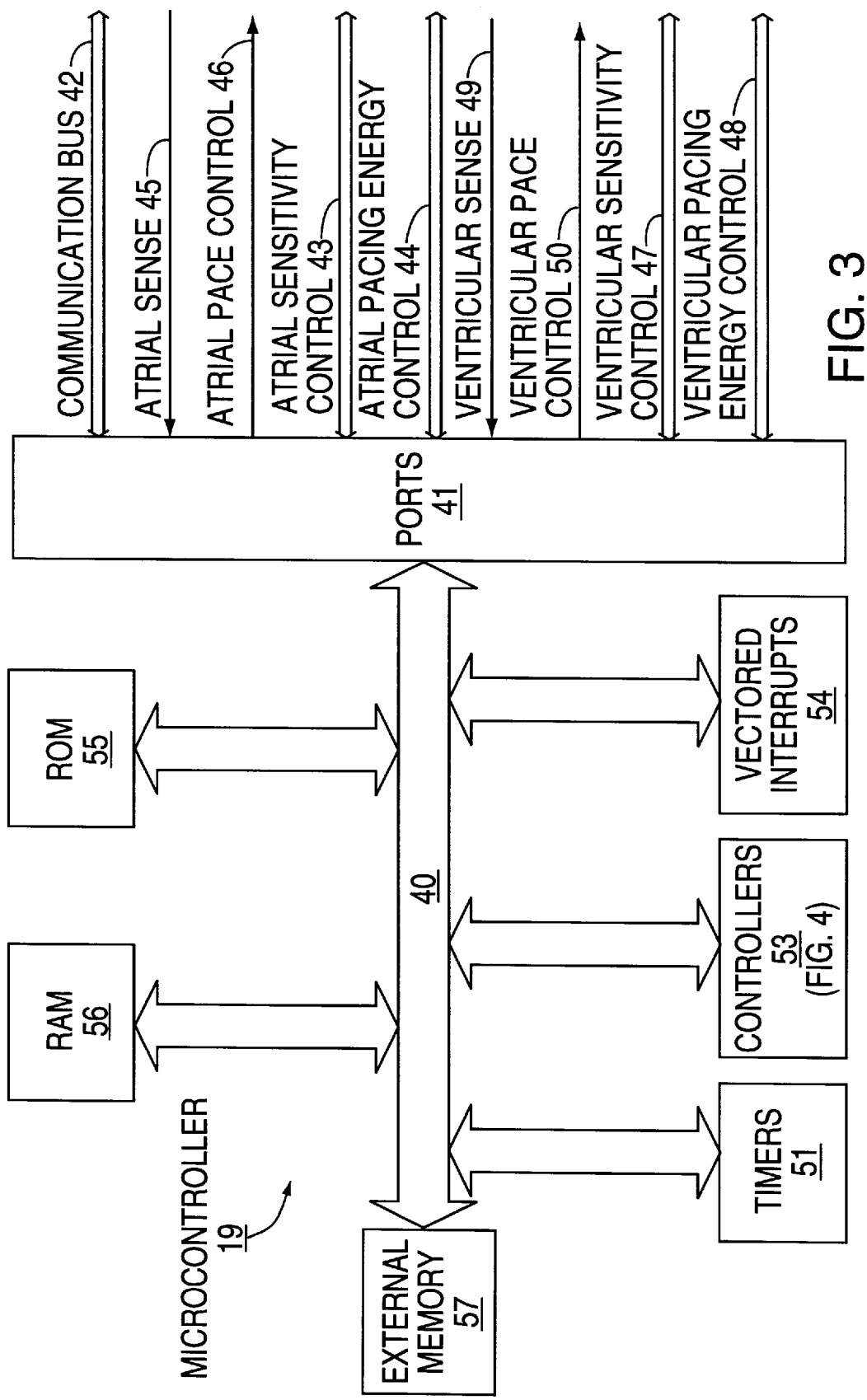
FIG. 3 shows a block diagram of a microprocessor for the pacemaker of FIG. 2.

FIG. 3 shows the microprocessor 19 having a timer circuit 51 for generating several timing signals on its output ports, a controller 53, a vectored interrupts circuit 54, a ROM 55, a RAM 56, an external memory 57 and an interface port 41. Signals between these elements are exchanged via an internal communications bus 40. Timer circuits generate various timing signals at its output ports. The RAM 56 acts as a scratchpad and active memory during execution of the programs stored in the ROM 55 and used by the microprocessor 19. ROM 55 is used to store programs including system supervisory programs, detection algorithms for detecting and confirming arrhythmias, and programming for determining the rate of the pacer, as well as storage programs for storing, in external memory 57, data concerning the functioning of the pulse generator 10 and the electrogram provided by the ventricular cardiac lead 13. The timer circuit 51, and its associated control software, implements some timing functions required by the microprocessor 19 without resorting entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communication bus 42 serves to provide signals indicative of such control to the microprocessor 19.

The microprocessor 19 through its port 41 receives status and/or control inputs from the pace and sense circuit 17, including the sense signals on the sense lines 45 and 490 previously described. Using controller 53, it performs various operations, including arrhythmia detection, and produces outputs, such a the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits. The rate of the atrial and/or ventricular pacing is adjusted by controller 53 as set forth below.

The pacemaker 10 of the present invention will function properly using any metabolic indicator rate system, so long as that system is able to reliably relate the sensed parameter to an appropriate matching of metabolic demand with the paced rate. However, the preferred embodiment of the invention employs the impedance measurement circuit 14, shown in FIG. 5, which measures the cardiac impedance to determine the respiratory minute volume as described generally in U.S. Pat. No. 4,901,725 to T. A. Nappholz, et al., issued Feb. 20, 1990 for "Minute Volume Rate-Responsive Pacemaker," incorporated herein by reference.

Figure 4:
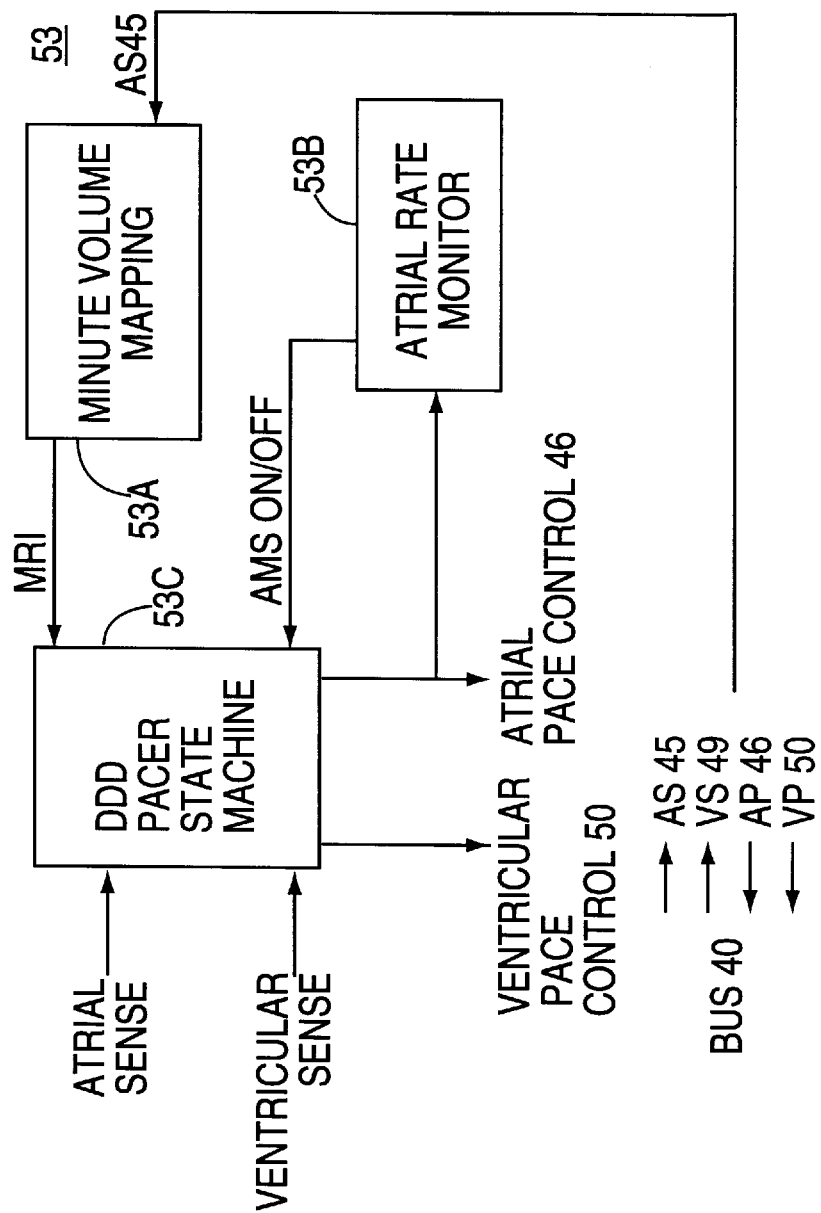
FIG. 4 shows details of the controller for the microprocessor of FIG. 3.

FIG. 4 shows the block diagram of the controller 53 of FIG. 3. The controller 53 includes a pacer 53C, which is preferably a state machine, a minute volume processor 53A and an atrial rate monitor 53B. The minute volume processor 53A uses the data supplied via the internal bus 40 and the communication bus 42 from the impedance measurement block 14 to relate the minute volume indicated by the impedance measurement to the Metabolic Rate Interval (MRI). This interval is then used by the pacer 53C to determine the length of each interval in the timing cycle. While the pacemaker 10 is preferably operating in a DDD mode, it should be understood that it can operate in other modes as well. The atrial rate monitor 53B generates an Automatic Mode Switching (AMS) signal upon detection of a non-physiological atrial rate and rhythm. This AMS signal automatically switches the pacemaker 10 to a non-atrial-tracking mode. When a physiological atrial rate resumes, the AMS signal is deactivated and the pacemaker returns to an atrial tracking mode.

Figure 5:
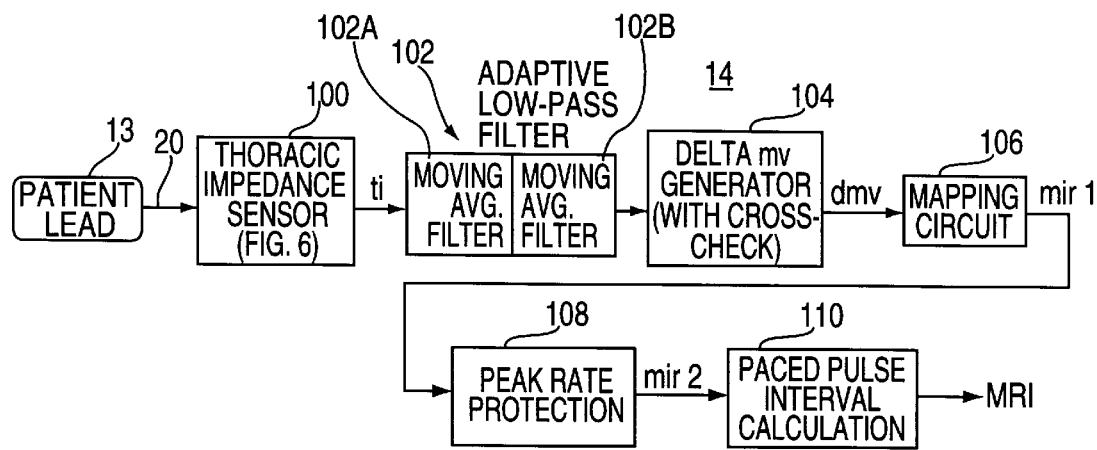
FIG. 5 shows details of the minute volume processor for the controller of FIG. 4.
Figure 10:
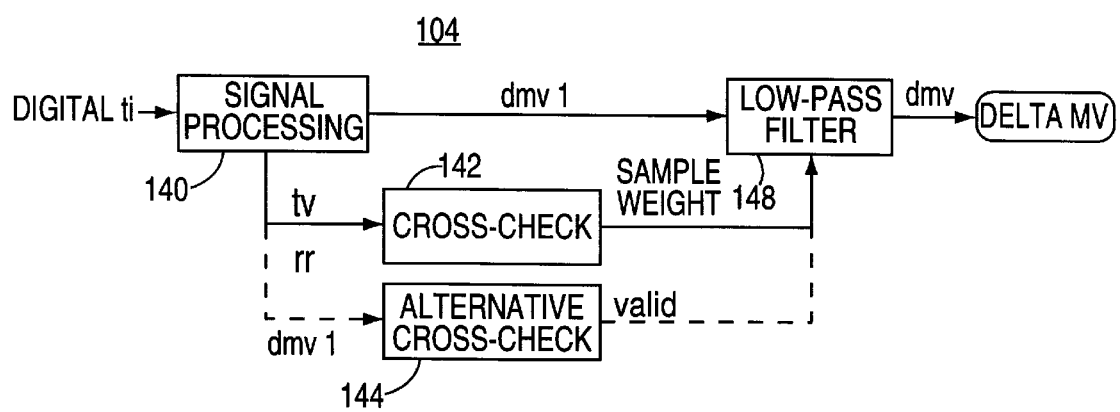
FIG. 10 shows details of the circuitry used to convert the thoracic impedance into a corresponding differential minute volume.

Referring now to FIG. 5, impedance measurement circuit 14 includes a thoracic impedance sensor 100 which is coupled by connection 20 to one of the patient's leads, such as lead 13. The sensor 100 generates a time-dependent signal ti indicative of the sensed thoracic impedance of the patient. The signal is fed to an adaptive low-pass filter 102 to eliminate stroke volume noise. Then the output from the low-pass filter is entered into a delta minute ventilation (dmv) generator 104 which converts this ti signal into a corresponding dmv signal as indicated in FIG. 10 and discussed in more detail below. The signal dmv is fed to a mapping circuit 106 which uses a conformal mapping (discussed in more detail below) to generate a corresponding metabolic indicated rate MIR1.

This signal MIR1 is fed to a peak rate protection circuit. The peak rate protection a circuit generates a second signal MIR2. This signal is fed to an interval calculator 110 which uses MIR2 to calculate the metabolic rate interval MRI discussed above.

Figure 6:
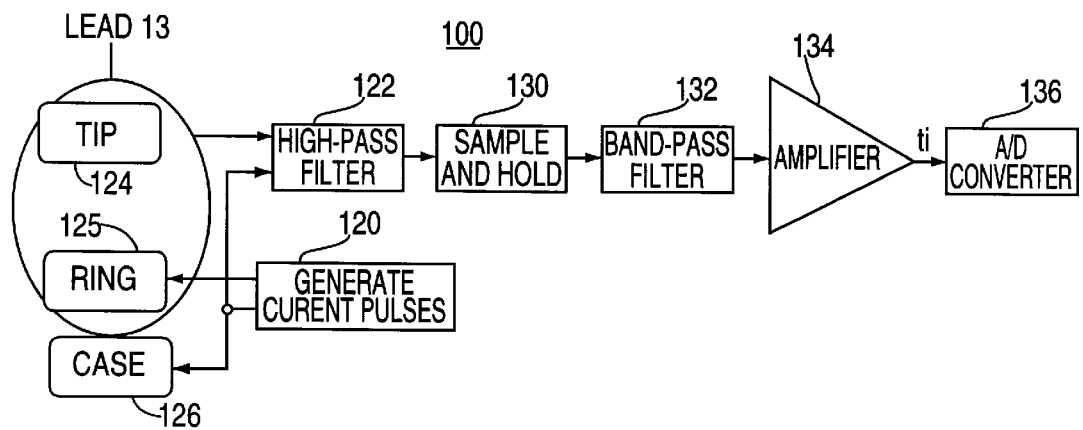
FIG. 6 shows a block diagram for the circuit used to determine thoracic impedance.

Referring now to FIG. 6, a known thoracic impedance sensor 100 includes a current generator 120 and a high pass filter 122 coupled to one of the patient leads, such as lead 13. (It should be clear that other leads may be used as well for determining the mv parameter as described, for example, in U.S. Pat. No. 5,562,712. The lead 13 includes a tip electrode 124 and a ring electrode 126. As known in the art, at predetermined times, the current generator 120 applies current pulses between the ring electrode 126 and pacemaker case 128, and the corresponding voltage is sensed between the tip electrode 124 and case 128. Typically, each current pulse has a pulse width of about 7.5 μsec, at repetition rate of about 18 pulses per second and an amplitude of about 1 mA. This pulse repetition rate is chosen at well about twice the Nyquist sampling rate for the highest expected intrinsic heart beats, and is preferable so that it can be easily differentiable from noise induced by a power line at 50 or 60 Hz.

The sensed voltage is passed through the high pass filter 122 selected to accept the 7.5 μsec pulses and exclude all noise signals. After filtering, the voltage signal is sampled by a sample and hold (S/H) circuit 130. Preferably the S/H circuit takes samples before the start of the test pulses from generator 120 (to enhance the effectiveness of the filter 122) as well as toward the end of the pulse duration.

The output of circuit 130 is passed through a band pass filter 132 which selects the signals i the range of normal respiration rate, which is typically in the range of 5–60 cycles/minute.

The output of the BPF 132 amplified by amplifier 134 to thereby generate the thoracic impedance signal ti. The amplifier raises the signal ti to a level sufficient so that it can be sensed and processed by the delta minute volume generator 104. This ti signal is then fed to an A/D converter 136 to generate a digital representation of the signal ti.

Figure 7A:
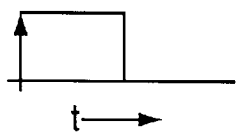
FIGS. 7A–7C show the time domain impulse response of an adaptive low pass filters 102A, and 102B, and the overall response respectively.
Figure 7B:
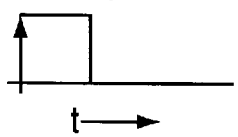
Figure 7C:
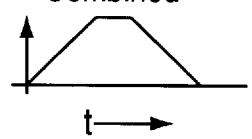
Figure 8A:
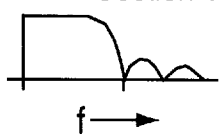
FIGS. 8A–8C show a frequency domain response corresponding to the time domain responses of FIGS. 7A–7C.
Figure 8B:
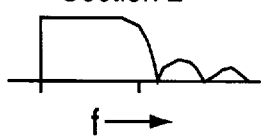
Figure 8C:
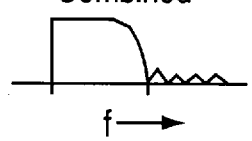

The adaptive low-pass filter 102 removes cardiac stroke volume artifact and other high-frequency noise and artifact signals from the tidal volume. It is preferably implemented as two cascaded moving-average filters 102A, 102B. The filters 102A, 102B are structured and configured to generate a very sharp cutoff with a notch at or near the cardiac stroke volume frequency. Each filter is formed with a digital accumulator (not shown). The following equations and FIGS. 7(A–C) and 8(A–C) describe the operation of the adaptive low-pass filter in the time and frequency domain.

$n1 = \text{int}(psi/dt + \frac{1}{2})$ $n2 = \text{int}(n1 * \frac{2}{3} + \frac{1}{2})$ a1 = sum (last n1 samples of fin)

a2 = sum (last n2 samples of a1)

n3 = sum (last n2 samples of n1)

fout = a2/n3 where n1 = number of samples in section 1 moving-average filter 102A n2 = number of samples in section 2 moving-average filter 102B;

n3 = number of samples averaged in both filter sections;

psi = pace or sense interval dt = time interval between iterations, typically about 47 milliseconds fin = input tidal volume, i.e., the input to the filter 102;

a1 = the sum in the accumulator of filter 102A;

a2 = the sum in the accumulator of filter 102B;

fout = output tidal volume generated by filter 102;

int = denotes the integer portion.

Figure 9A:
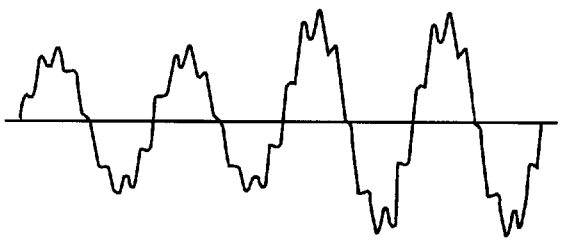
FIGS. 9A–9B show the thoracic impedance input and the corresponding adaptive filter output.
Figure 9B:
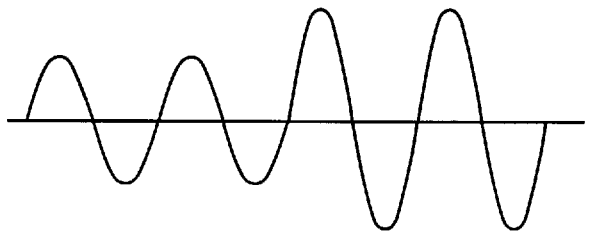

FIGS. 9A and 9B show analog waveforms of the intermediate signals generated. FIG. 9A shows the input to the adaptive low-pass filter and, FIG. 9B shows the output of filter 102.

Referring to FIG. 10, the delta mv calculation circuit 104 includes a signal processing block 140, a cross check circuit 142, a low-pass filter 148, and a low-pass filter 148. Circuit 104 is best implemented by a microprocessor, however it is shown here as discrete circuits for the sake of clarity.

The computer circuit 140 calculates an instantaneous minute volume (dmv1) every 1.5 seconds, with also possibly separately tidal volume (tv) and respiration rate (rr), dependent upon the implementation. See U.S. Pat. No. 4,901,725 and the applications listed above.

If the implementation is done in a breath-by-breath basis, the parameters rr, tv and dmv1 (respiratory rate, tidal volume and delta minute volume) are computed. Details of a method of calculating rr, dmv1, tv are disclosed for example in copending application Ser. No. 08/850,557 filed May 2, 1997, entitled RATE-RESPONSIVE PACEMAKER WITH RAPID MINUTE VOLUME DETERMINATION, filed on even date herewith, and incorporated herein by reference. The method disclosed in this reference does not form part of this application. Other methods may be used as well.

Figure 11A:
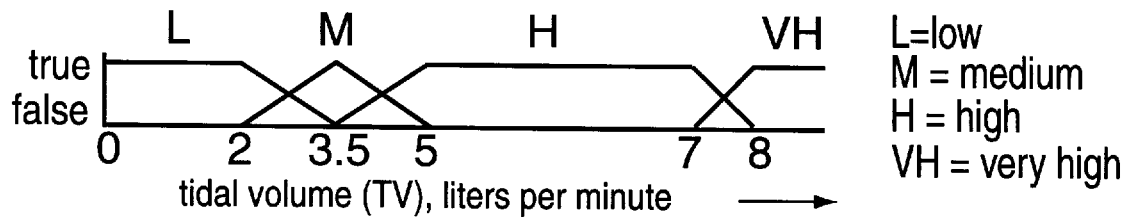
FIGS. 11A and 11B show the membership functions used by a fuzzy logic diagram for a cross check for FIG. 10.
Figure 11B:
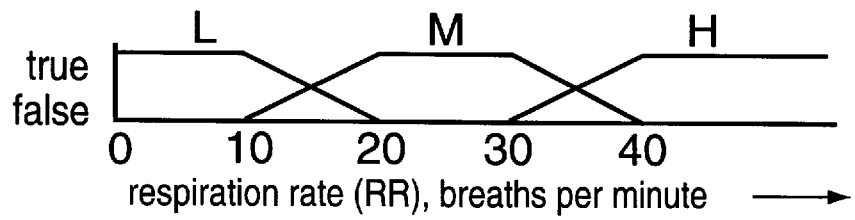
Figure 11C:
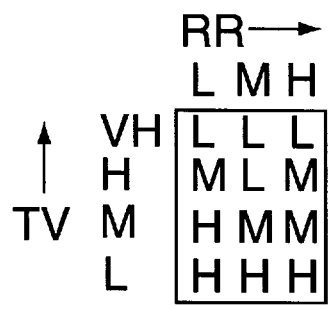
FIG. 11C shows a truth table defining the cross check confidence rule for the cross-check circuit.

These parameters are then passed through a cross-check circuit 142 (FIG. 10). The cross-check circuit 142 compares tidal volume tv and respiration rate rr to develop an estimate of confidence and a sample weight for each minute ventilation value dmv1. Preferably, circuit 142 is implemented as a fuzzy logic circuit. FIG. 11A shows the input membership function for circuit 142 used for the tidal volume (tv) while FIG. 11B shows the input membership function for the respiration rate (rr). As can be seen in these Figures, the tidal volume is associated with four values: low (L), medium (M), high (H) and very high (VH). The respiration rate is associated with three values: low (L), medium (M), and high (H). The confidence rule relating these two functions is shown in FIG. 11C.

Figure 11D:
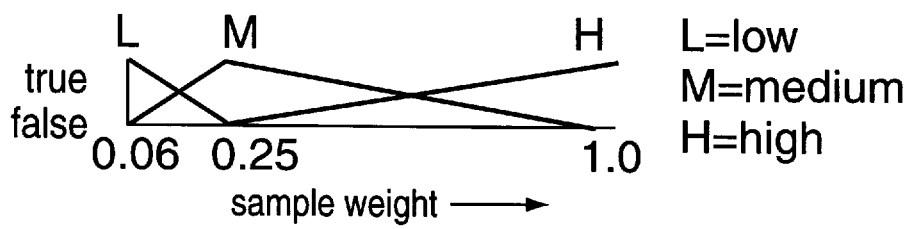
FIG. 11D shows the output membership functions of the cross-check circuit.

Circuit 142 generates an output designated sample weight. The membership for this output is shown in FIG. 11D for three values: low (L), medium (M) and high (H). For the rule base and membership functions illustrated in FIGS. 11A, 11B, 11C, 11D have been found to function effectively. Preferably, a center-of-area (COA) decomposition is used as a defuzzification function to compute the numerical value of sample weight. However, other methods may be used to simplify computation.

The method for signal cross-check 142 performs well only when both tidal volume (tv) and respiration rate (rr) are both generated as expressed above. For other methods for computing delta minute ventilation which does not compute tv and rr directly, this methodology would not be compatible.

Figure 12A:
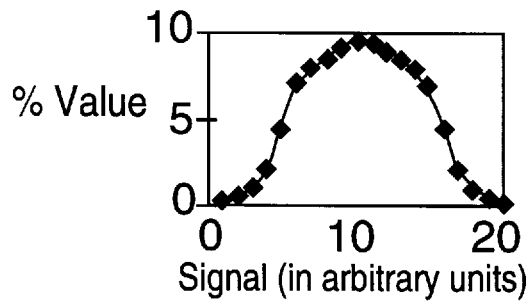
FIG. 12A shows the histograms utilized in the alternative cross-checking algorithm.
Figure 12B:
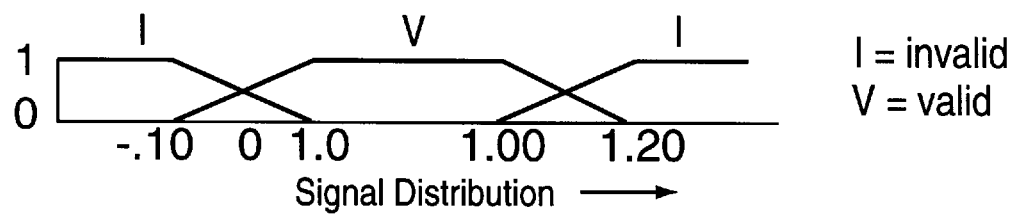
FIG. 12B shows the output membership functions for the alternative cross-checking algorithm.

Instead, an alternative signal cross-check algorithm 144 may be utilized in place of the cross-check 142 algorithm. The signal generated, the derivative of the raw thoracic impedance can be placed onto a cumulative histogram as shown in FIG. 12A. Then, signal values representing the 0, 10, 90, and 100 percentile of the histogram can be generated. The −10 percent and 120 percent values can be computed by the following formulas:

Val (−10%)=min (0, Val (0%)−(Val(10%)−Val(0%))
Val (110%)=Val (100%)+(Val (100%)−Val (90%))
Val (120%)=Val (100%)+2*(Val (100%)−Val (90%))
Val (x%)=x percentile value as determined by the histogram Then the signal generated is inputted through the following output membership function as shown in FIG. 12B. The output is a number between 0 to 100% based upon membership in the VALID category. This number is then entered into a multiplier 148 with the computed dmv1 from 140 for further processing.

Returning to FIG. 10, the weighted delta minute ventilation value of dmv1 is passed through the low-pass filter 148 to smooth the results. The time constant of this filter is variable, according to the sample weight parameter computed by the cross-check circuit 142 described above. Preferably, the filter 148 is a single pole low-pass filter, which has been found to model physiological response more closely than more complex filters. The filter is implemented preferably digitally, for example, by using the equations given below. In a fixed-point arithmetic implementation an accumulator (incorporated in filter 148, not shown) must have more bits of precision than the delta minute ventilation values. The accumulator range is limited to prevent the filter from exhibiting delayed response following very high or very low input values.

a=a+(dmv1−a)*(w*dt/tc)
if (a>max_dmv)a=max_dmv
if (a<0)a=0 where:
dmv=a
dmv1=input (unfiltered delta minute ventilation from the circuit 140)
dmv=output (filtered delta minute ventilation)
a=the sum in the filter accumulator
w=sample weight
dt=time interval between iterations, typically 1.5 seconds
tc=time constant, typically 12 seconds
max_dmv=the value of dmv which will map to max_hr (discussed more fully below).

The output then of filter 148 is the delta minute volume parameter dmv in FIG. 5. Next, this parameter dmv must be converted into a metabolic indicated rates (MIR) parameter. Schemes for performing this function are well known in the art. One such scheme is disclosed in copending application Ser. No. 08/641,223 filed Apr. 30, 1996, entitled RATE RESPONSIVE PACEMAKER WITH AUTOMATIC RATE RESPONSE FACTOR SELECTION and its continuation, U.S. application Ser. No. 08/823,077 filed Mar. 24, 1997, incorporated herein by reference. As disclosed in this reference, a curvilinear mapping between minute ventilation and MIR is preferable because it can be modeled after physiological data on a wide range of normal subjects.

Figure 13:
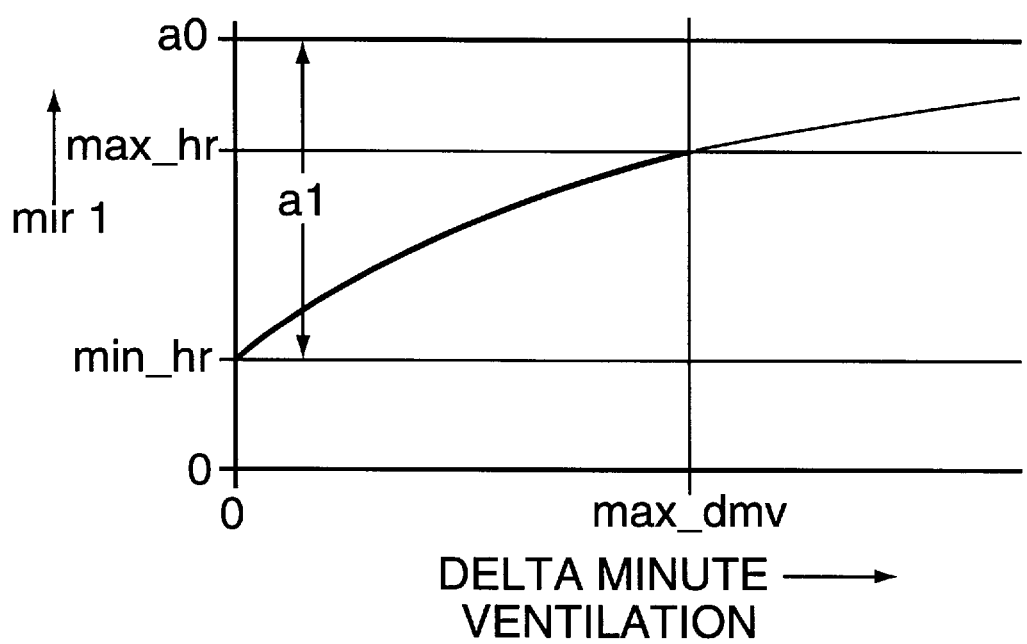
FIG. 13 shows an exponential mapping function mapping delta minute ventilation to MIR.

More particularly, it has been found that an excellent fit can be generated if an exponential mapping function is used. One such function is shown in FIG. 13. To save computational time, the exponential function may be performed by an interpolated table look-up function. The logarithmic function used to compute max_dmv is evaluated only by the programmer, at the time min_hr or max_hr is changed. The rate response factor (RRF) is defined so that one unit change in RR relates to a 10% change in the peak value minute ventilation signal. It may be computed and displayed by the programmer, or may be entered by the user to initialize mv_gain.

The mapping function of FIG. 13 is defined by the following:

MIR1=a0−a1*exp (−dmv/a2)
max_dmv=a2*ln(a1/(a0−max_hr)) (used by low-pass filter 148)
a0=230 pulses per minute (a0 is the upper heart rate asymptote)
a1=a0−min_hr (a1 determines min_hr)
a2=133 pulses per minute (a2 determines the hr/mv slope)
dmv=filtered delta minute ventilation from delta mv generator 102
max_dmv=the maximum value of dmv which is mapped to max_hr
max_hr=the programmed maximum value of paced heart rate
RRF=rrf_const+ln(mv_gain/max_dmv)/ln(1.1)
mv_gain=max_dmv*1.1^(RRF-rrf_const)
rrf_const is chosen to establish the nominal RRF value.

Figure 14A:
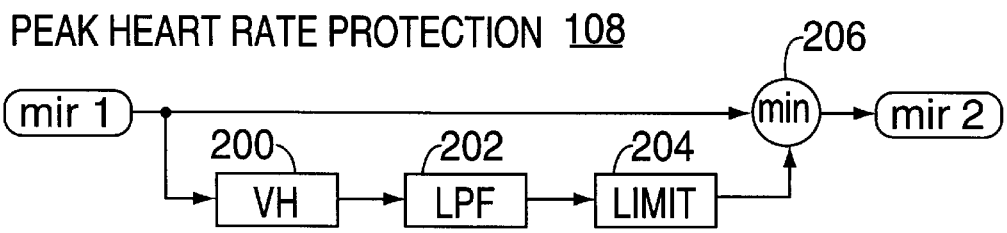
FIG. 14A shows a block diagram for the peak heart rate protection circuit 108.
Figure 14B:
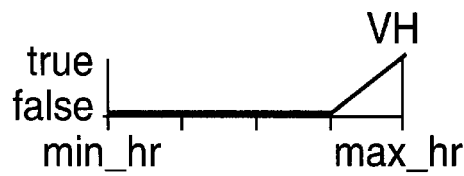
FIG. 14B shows the input membership function for the diagram of FIG. 14A.

As indicated in FIG. 5, the parameter MIR1 is also fed to a peak rate protection circuit 108 (FIG. 5). This function allows the user to specify the maximum duration for pacing at the maximum rate. It is intended to prevent extended pacing at or near the maximum heart rate following a change in the magnitude of the thoracic impedance signal, due to excessive noise or patient physiological change. Preferably, the peak rate protection circuit is a fuzzy logic circuit shown in more detail in FIG. 14. The circuit includes a very high or near peak determinator 200, described by the membership function of FIG. 14B, a low pass filter 202 a limiter 204 and a minimum selector 206.

The low-pass filter 202 is a single-pole infinite impulse response filter having a time constant which is the maximum continuous time during which peak rate pacing is allowed. A reasonable range for the programmable time constant is from 30 minutes to 8 hours, and off.

Figure 14C:
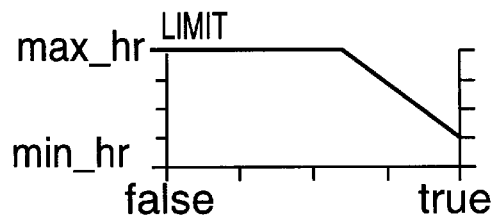
FIG. 14C shows the output membership function for the diagram of FIG. 14A.

The function of the limiter 204 is to generate a limit to the paced heart rate. The limit is equal to the maximum heart rate if the low-pass filter output is less than 63% true. It then decreases to 25% of the maximum heart rate elevation if the low-pass filter output is 100% true. If the input heart rate (MIR1) abruptly reaches the maximum heart rate, the output (MIR2) should remain at maximum for the time constant of the low-pass filter, and then smoothly decreases toward a final value of 25% of the maximum heart rate elevation. The membership function for the limiter 204 is shown in FIG. 14C.

The output of limiter 204 and the signal MIR1 are fed to minimum selector 206 as shown. This selector 206 then generates an output MIR2 which is the lower of the input (MIR1) and the limit generated by the limiter 204.

Returning to FIG. 5, the parameter MIR2 is then used to generate a metabolic indicated rate interval (MRI) by calculator 110. The paced pulse interval is inversely related to the paced heart rate as indicated by the following equation.

ppi=60000/phr ppi=paced pulse interval, milliseconds phr=paced heart rate, pulses per second Other time intervals of the pacing cycle are computed by the state machine 53C (FIG. 4) using the paced pulse interval and/or the heart rate.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

We claim:

1. A rate responsive implantable pacemaker comprising:

a cardiac sensor for sensing cardiac activity and for generating a cardiac activity signal;

a pace generator for generating pacing pulses in response to pacing commands;

a parameter sensor for sensing a metabolic demand parameter;

a parameter processing circuit for processing said metabolic demand parameter to generate a metabolic indicated parameter, said processing circuit including an adaptive filter for removing from said metabolic demand parameter undesirable artifacts and an intermediate calculator for generating intermediate parameters and a cross check circuit for performing a cross check between said intermediate parameters and said metabolic demand parameter; and a controller receiving said cardiac activity signal and said metabolic indicated parameter for generating said pacing commands.

2. The pacemaker of claim 1 wherein said artefacts include stroke volume noise.

3. The pacemaker of claim 1 wherein said adaptive filter includes a sample and hold circuit for sampling said metabolic demand parameter and an average calculator for generating a moving average of the samples.

4. The pacemaker of claim 1 wherein said adaptive filter includes two cascaded filter sections configured with a sharp cutoff and a notch near the cardiac stroke volume frequency.

5. The pacemaker of claim 1 wherein said intermediate parameters include a respiration rate and a tidal volume.

6. The pacemaker of claim 5 wherein said intermediate parameters include a derivative of said metabolic demand parameter.

7. The pacemaker of claim 6 wherein said Processing means includes a histogram generator for generating a histogram of said derivative, said histogram being used to generate said cross check circuit.

8. The pacemaker of claim 1 wherein said cross check circuit comprises a fuzzy logic circuit.

9. A rate responsive implantable pacemaker comprising:

a cardiac sensor for sensing cardiac activity and for generating a cardiac activity signal;

a pace generator for generating pacing pulses in response to pacing commands;

a parameter sensor for sensing a metabolic demand parameter;

a parameter processing circuit for processing said metabolic demand parameter to generate a metabolic indicated parameter; and a controller receiving said cardiac activity signal and said metabolic indicated parameter for generating said pacing commands; said controller including a high rate protection circuit for protecting the patient against high pacing rates, said high rate protection circuit including a fuzzy logic rate limiter for limiting said metabolic indicated parameter to a safe range;

said controller further including an intermediate calculator for generating intermediate parameters and a crosscheck for performing a cross check between said intermediate parameters and said metabolic demand parameter.

\* \* \* \* \*